(12) United States Patent
Stern et al.

(10) Patent No.: US 8,013,300 B2
(45) Date of Patent: Sep. 6, 2011

(54) SAMPLE DECONTAMINATION

(75) Inventors: Lewis A. Stern, Hollis, NH (US); Louis S. Farkas, III, Durham, NH (US); Billy W. Ward, Merrimac, MA (US); William DiNatale, Bedford, MA (US); John A. Notte, IV, Gloucester, MA (US); Lawrence Scipioni, Bedford, MA (US)

(73) Assignee: Carl Zeiss NTS, LLC, Peabody, MA (US)

( * ) Notice: Subject to any disclaimer, the term of this patent is extended or adjusted under 35 U.S.C. 154(b) by 236 days.

(21) Appl. No.: 12/470,316

(22) Filed: May 21, 2009

(65) Prior Publication Data
US 2009/0314939 A1   Dec. 24, 2009

Related U.S. Application Data

(60) Provisional application No. 61/074,495, filed on Jun. 20, 2008.

(51) Int. Cl.
*H01J 49/14* (2006.01)
*G21K 5/00* (2006.01)

(52) U.S. Cl. ............ 250/307; 250/492.3; 250/492.21; 250/423 R; 250/424

(58) Field of Classification Search ............ 250/307, 250/492.3, 492, 21, 423 R, 424; 313/362.1
See application file for complete search history.

(56) References Cited

U.S. PATENT DOCUMENTS

| 4,950,498 | A | 8/1990 | Kaito |
| 5,236,562 | A | 8/1993 | Okumura et al. |
| 5,981,001 | A * | 11/1999 | Komatsu et al. ............ 427/582 |
| 6,110,825 | A | 8/2000 | Mastromatteo et al. |
| 6,891,171 | B1 | 5/2005 | Hagiwara et al. |
| 7,141,859 | B2 * | 11/2006 | DeBoer et al. ............ 257/414 |
| 7,375,328 | B2 * | 5/2008 | Yonezawa et al. ........... 250/310 |
| 2002/0053353 | A1 | 5/2002 | Kawata et al. |
| 2006/0138363 | A1 | 6/2006 | Yonezawa et al. |
| 2007/0080307 | A1 | 4/2007 | Bruijn et al. |
| 2007/0158558 | A1 | 7/2007 | Ward et al. |
| 2007/0194228 | A1 | 8/2007 | Frosien et al. |
| 2007/0259293 | A1 | 11/2007 | Shin et al. |
| 2007/0259474 | A1 | 11/2007 | Shin et al. |
| 2008/0029835 | A1 | 2/2008 | Beckert et al. |
| 2010/0051805 | A1 * | 3/2010 | Rahman et al. ............ 250/307 |

FOREIGN PATENT DOCUMENTS

| GB | 2 352 323 | 1/2001 |
| GB | 2 358 955 | 8/2001 |
| JP | 12-90758 | 11/1989 |
| JP | 11-162391 | 6/1999 |

OTHER PUBLICATIONS

Livengood et al., "Helium ion microscope invasiveness and imaging study for semiconductor applications," J. Vac. Sci. Technolog., 25(6):2547-2552, (2007).

* cited by examiner

*Primary Examiner* — Nikita Wells
(74) *Attorney, Agent, or Firm* — Fish & Richardson P.C.

(57) ABSTRACT

Disclosed herein are methods that include: (a) exposing a sample in a chamber to a first gas, where the first gas reacts with surface contaminants on the sample to form a second gas; (b) removing at least a portion of the second gas from the chamber; and (c) exposing the sample to a charged particle beam to cause a plurality of particles to leave the sample and detecting at least some of the plurality of particles. The charged particle beam can include particles having a molecular weight of 40 atomic mass units or less.

19 Claims, 3 Drawing Sheets

US 8,013,300 B2

SAMPLE DECONTAMINATION

CROSS-REFERENCE TO RELATED APPLICATIONS

This application claims priority under 35 U.S.C. §119(e)(1) to U.S. Provisional Application No. 61/074,495 filed Jun. 20, 2008. The contents of this application is hereby incorporated by reference in its entirety.

TECHNICAL FIELD

This disclosure relates to exposing samples to charged particles, and in particular, to imaging samples with charged particles.

BACKGROUND

Samples can be exposed to charged particles for a variety of applications, including sample imaging. If contaminants are present on the surface of a sample during imaging, the quality of the images of the sample can be reduced.

SUMMARY

In general, in one aspect, the disclosure features a method that includes: (a) exposing a sample in a chamber to a first gas, where the first gas reacts with surface contaminants on the sample to form a second gas; (b) removing at least a portion of the second gas from the chamber; and (c) exposing the sample to a charged particle beam to cause a plurality of particles to leave the sample and detecting at least some of the plurality of particles. The charged particle beam includes particles having a molecular weight of 40 atomic mass units or less.

In another aspect, the disclosure features a method that includes exposing a sample to a charged particle beam to cause a plurality of particles to leave the sample and detecting at least some of the plurality of particles, and, during exposure of the sample to the charged particle beam, exposing the sample to a first gas, where the first gas reacts with surface contaminants on the sample to form a second gas, and removing at least a portion of the second gas from the chamber.

In a further aspect, the disclosure features a method that includes: (a) exposing a sample in a chamber to ozone, where the ozone reacts with surface contaminants on the sample to form volatile reaction products; (b) removing at least a portion of the volatile reaction products from the chamber; and (c) exposing the sample to a helium ion beam to cause a plurality of particles to leave the sample and detecting at least some of the plurality of particles.

Embodiments can include one or more of the following features.

The first gas can be ozone. The surface contaminants can include hydrocarbons.

A background pressure in the chamber during exposure of the sample to the first gas an be less than atmospheric pressure.

The sample can be exposed to the first gas during exposure of the sample to the charged particle beam. Alternatively, or in addition, the sample can be exposed to the first gas to form a second gas prior to exposing the sample to the charged particle beam, and at least a portion of the second gas can be removed from the chamber. Alternatively, or in addition, the sample can be exposed to the first gas in a region outside the chamber prior to exposing the sample to the charged particle beam in the chamber.

The plurality of particles can include secondary electrons. Alternatively, or in addition, the plurality of particles can include scattered ions. The charged particle beam can include noble gas ions (e.g., helium ions).

The charged particle beam can include particles having a molecular weight of 20 atomic mass units or less (e.g., 4 atomic mass units or less).

The method can include forming the first gas by introducing gas particles into an activation apparatus, and activating the gas particles to form the first gas. The activation apparatus can include one or more electrodes, and activating the gas particles can include applying electrical potentials to at least some of the electrodes. Alternatively, or in addition, activating the gas particles can include exposing the gas particles to an electromagnetic field in the activation apparatus. The electromagnetic field can include ultraviolet light.

The method can include producing the charged particle beam in a gas field ion source. The gas field ion source can include a tip configured to produce an electric field that ionizes gas molecules to form the charged particle beam, and the first gas can be prevented from contacting the tip.

The method can include forming an image of the sample based on the detected particles, where a maximum dimension of a field of view of the image is 10 microns or less (e.g., one micron or less). A spot size of the charged particle beam at a surface of the sample is 50 nanometers or less (e.g., 5 nanometers or less).

The method can include forming an image of the sample based on the detected particles, where a resolution of the image is 5 nm or smaller (e.g., 3 nm or smaller).

The method can include, prior to exposing the sample to the first gas: (a) exposing the sample to the charged particle beam to cause a plurality of particles to leave the sample, detecting at least some of the plurality of particles, and forming an image of the sample based on the detected particles; and (b) analyzing the image to identify at least some of the surface contaminants.

The method can include, prior to exposing the sample to the first gas: exposing the sample to the charged particle beam to cause a plurality of particles to leave the sample, detecting at least some of the plurality of particles, and identifying at least some of the surface contaminants based on the detected particles.

A maximum interval during which the sample is not exposed to the first gas during exposure of the sample to the charged particle beam is five minutes or less.

The method can include exposing one or more internal surfaces of the chamber to the first gas, where the first gas reacts with contaminants on the one or more internal surfaces of the chamber to form a third gas, and removing at least a portion of the third gas from the chamber. The contaminants on the one or more internal surfaces of the chamber can include hydrocarbons.

The charged particle beam can include electrons.

A pressure of ozone in the chamber is $10^{-6}$ Torr or more (e.g., $10^{-5}$ Torr or more).

The charged particle beam can include gallium ions.

The charged particle beam can include ions having a molecular weight of 40 atomic mass units or less.

The method can include, before exposing the sample to the first gas: (a) forming a plasma, and exposing the sample to the plasma outside the chamber, where the plasma reacts with surface contaminants on the sample to form products; and (b) removing at least a portion of the products from the sample surface. The method can further include introducing the sample into the chamber.

Embodiments can include one or more of the following advantages.

In some embodiments, sample decontamination can occur continuously, even while the sample is being imaged via exposure to an ion beam. A reactive gas can be delivered to decontaminate the sample in a manner such that significant disruption of the incident ion beam does not occur. As a result, progressive contamination of the sample as a result of contaminant deposition and/or beam-induced reactions that produce contaminants can be reduced and/or eliminated. Distortions, errors, and other undesired effects in images of the sample which result from such contaminants can be reduced and/or eliminated.

In certain embodiments, continuous introduction of the reactive gas can maintain a higher level of cleanliness in the chamber than would otherwise occur in the absence of the reactive gas, because contaminants on interior chamber surfaces can also be volatilized and removed via reaction with the reactive gas.

In some embodiments, a reactive gas such as ozone can be generated in situ or in a dedicated external gas source, from a relatively common, inexpensive feed gas such as oxygen or air. As a result, the sample decontamination system can be inexpensive to operate, and can remain in operation even during periods where no sample is present in the chamber to maintain chamber cleanliness.

In certain embodiments, by reducing and/or eliminating surface contaminants, images of samples can include enhanced surface contrast and fewer imaging errors. In particular, relatively light ion beams such as helium ion beams, hydrogen ion beams, neon ion beams, and argon ion beams produce images which are especially sensitive to sample surface structure. By reducing and/or eliminating surface contaminants, the benefits of the enhanced sensitivities of such ion beams can be realized, particularly during high-magnification imaging of samples.

In some embodiments, the configuration of various ion optical elements (e.g., filters, apertures, lenses, and other field-generating elements) prevents reactive gas particles such as ozone molecules from entering the ion source (and in particular, from contacting the electrically conductive tip in the ion source which generates the ion beam). As a result, the ion source is not degraded by the reactive gas, and can operate stably for extended periods of time.

The details of one or more embodiments are set forth in the accompanying drawings and the description below. Other features and advantages will be apparent from the description, drawings, and claims.

DETAILED DESCRIPTION

Figure 1:
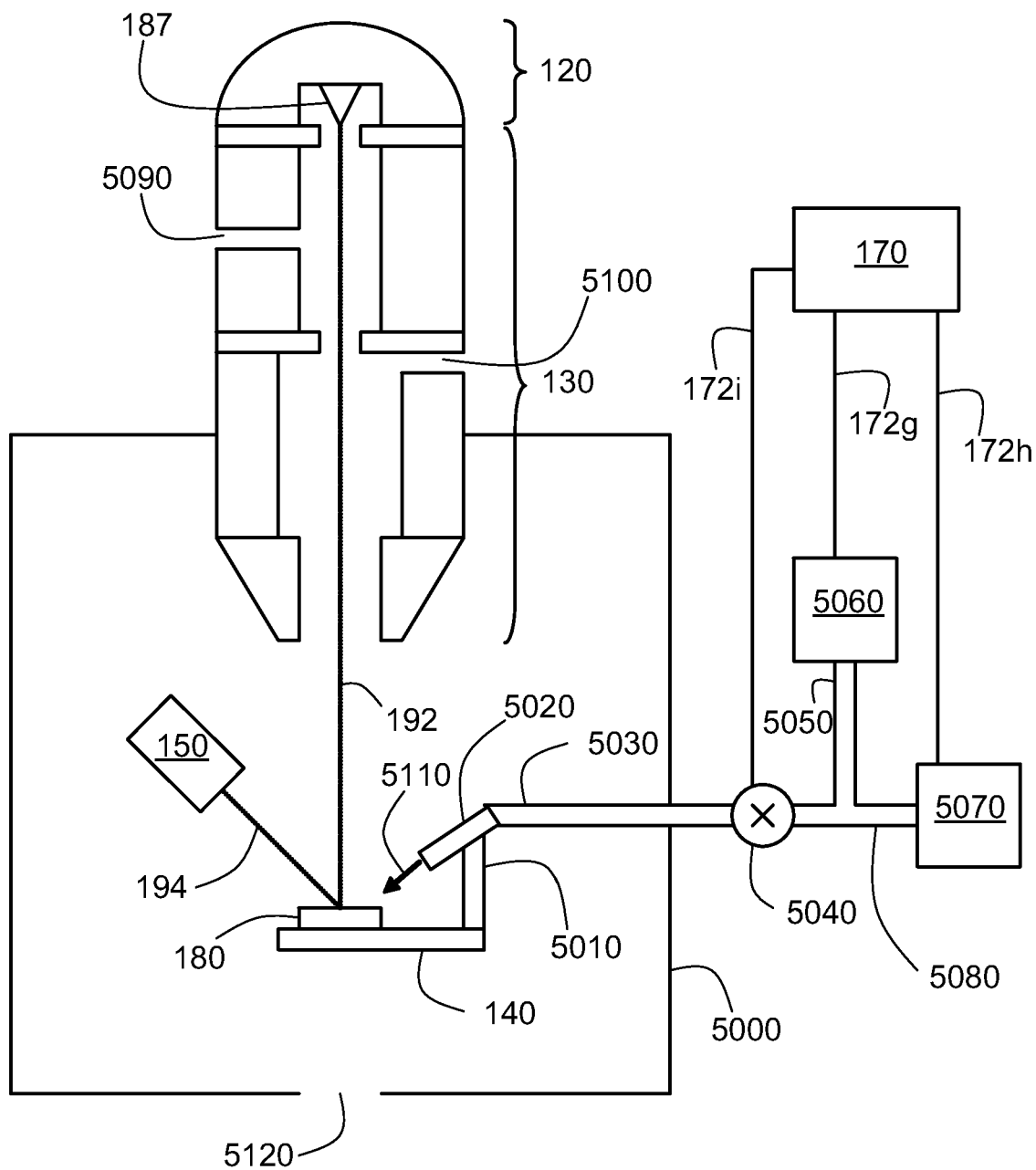
FIG. 1 is a schematic diagram showing a chamber that includes a reactive gas delivery system.

Ion beam imaging of samples can provide images with high resolution, high magnification, and high contrast, enabling detailed and accurate characterization of sample surface properties and properties relating to sub-surface sample layers. During ion beam imaging, a sample is exposed to ions from an ion beam, causing one or more different types of particles (e.g., secondary electrons, scattered electrons, secondary ions, scattered ions, photons) to leave the sample in response to the incident ions. One or more detectors are positioned to detect the particles that leave the sample, and sample images can be formed based on the detected particles.

Typically, ion beam imaging is performed in a chamber at reduced pressure (e.g., at an ambient pressure in the chamber that is less than atmospheric pressure). The chamber is sealed to prevent contamination of the sample and also to reduce spurious detector signals that result from detection of contaminants. However, contaminants can still be present in the chamber even if the chamber remains sealed during imaging. For example, contaminants can be present on the sample when the sample is introduced into the chamber. Alternatively, or in addition, contaminants can be generated when the sample is exposed to the ion beam by virtue of a reaction between ions in the ion beam and atoms of the sample. Further, contaminants can be introduced into the chamber by the pumping systems that are used to maintain reduced ambient pressure in the chamber.

Contaminants in the chamber can be detected by the detectors, producing spurious signals that degrade the resolution and/or contrast in sample images. Alternatively, or in addition, contaminants can be disposed on the surface of the sample that is being imaged, leading to imaging errors and/or obfuscation of the structure of the sample surface underlying the contaminants. In certain imaging modalities, such as voltage contrast imaging, surface contaminants can change the properties (e.g., the electrical properties) of the surface that is imaged, producing inaccurate and/or misrepresentative imaging results.

In general, limited surface contamination—and in particular, the presence of hydrocarbon contaminants on sample surfaces—during imaging is not as severe a problem during electron beam imaging of samples (e.g., in scanning electron microscopes) as it is during ion beam imaging of samples, because incident electrons are not as sensitive to the surface of the sample as ion beams. That is, the particles which leave the sample, typically secondary electrons, in response to an incident electron beam are produced from relatively deeper within the sample than particles which leave a sample in response to an incident ion beam. As a result, the distribution of particles which leave the sample following electron beam exposure is not as strongly influenced by the presence of surface contaminants on the sample during exposure to the electron beam. Moreover, although contaminants can be produced from a sample itself by chemical reactions initiated by exposing the sample to a beam of charged particles, electrons typically are less efficient (and, in many cases, significantly less efficient) at producing such surface contaminants than ion beams.

Further, in general, when samples are imaged by exposure to relatively heavy ions (e.g., with molecular weights of 41 atomic mass units or more), limited surface contamination during imaging is generally not a severe problem. Most likely, an observed absence of significant imaging errors in such cases is due to the sputtering away of such contaminants from the sample surface during exposure of the sample to the relatively heavy ions (e.g., gallium ions). Such sputtering can, under certain circumstances, remove sample surface atoms and/or layers, producing undesired modification of the sample.

Ion beams formed of relatively light ions, however, are typically more sensitive to the surface of a sample during imaging than ion beams formed of heavier ions or electron beams, due to reduced sputtering by the lighter ions and because secondary electrons generated by the incident ions are generated nearer to the surface of the sample than secondary electrons that are generated by incident electron beams. It has been discovered that as a result—and particularly, when high magnification images are acquired—surface contaminants reduce the accuracy and contrast of the images to a significantly greater extent than in electron beam or heavy ion imaging of samples. In particular, in ion microscopy, image contrast can be dependent on magnification, with decreasing contrast at higher magnification. For relatively light ion beams such as helium ion beams, this reduction in image contrast at high magnification is attributable in large measure to the presence of surface contaminants on the sample. That is, because a relatively large dose of ions is incident on a relatively small and contaminated portion of a surface, the overall magnitude of the effects of the contaminants on the images that are obtained can be very large. This heretofore unappreciated problem presents a significant obstacle to obtaining useful and quantitatively accurate images of certain types of samples.

Sample Decontamination

To assist in removing surface contaminants from a sample, one or more reactive gases such as ozone can be introduced into the reduced pressure chamber. The gas that is introduced reacts with surface contaminants, generating volatile reaction products which can then be removed from the chamber via conventional pumping, for example. FIG. 1 shows a schematic diagram of a sample chamber 5000 that includes a reactive gas delivery system. Chamber 5000 includes a gas field ion source 120 that includes an electrically conductive tip 187 that generates an ion beam 192 by producing an electric field that ionizes particles of a supply gas. Chamber 5000 also includes ion optics 130 that direct ion beam 192 to be incident on a surface of sample 180, and a sample manipulator 140 that supports sample 180. Ion optics 130 include a source pump outlet 5090 and a column pump outlet 5100, each of which is in fluid connection with a pump (e.g., a turbomolecular pump) to maintain reduced ambient pressure at source 120 and in ion optics 130, respectively.

Ion beam 192 causes a plurality of particles 194 to leave sample 180. Particles 194 can include one or more different types of particles such as, for example, scattered ions, secondary electrons, secondary ions, and photons. Detector 150 is positioned to detect particles 194 that leave sample 180.

Sample manipulator 140 includes a support 5010 that supports a reactive gas delivery tube 5020. Delivery tube 5020 is in fluid communication with a supply conduit 5030. Gas flow through supply conduit 5030 is controlled by regulator 5040. One or more reactive gases are introduced into supply conduit 5030 by reactive gas supply 5070 via tube 5080, which is in fluid communication with supply conduit 5030. Pump 5060, which is in fluid communication with tube 5080 through tube 5050, removes waste gases from tube 5080.

Electronic control system 170 is in electrical communication with regulator 5040, pump 5060, and gas supply 5070 via control lines 172*i*, 172*g*, and 172*h*, respectively, and controls the operation of these devices. By controlling gas supply 5070 and/or regulator 5040 and/or pump 5060, for example, electronic control system 170 can adjust the rate and/or composition of reactive gas supplied to chamber 5000. As shown in FIG. 1, delivery tube 5020 is positioned to direct reactive gas 5110 onto sample 180 in the vicinity of ion beam 192.

Chamber 5000 is in fluid communication with a chamber pump (not shown in FIG. 1) through outlet 5120. During operation, reactive gas 5110 (e.g., ozone) reacts with surface contaminants on sample 180, generating a variety of different volatile reaction products in the form of a product gas. The product gas is removed from chamber 5000 via outlet 5120 by the chamber pump.

In some embodiments, operation of the ion beam is interrupted for sample cleaning cycles, during which sample 180 is exposed to reactive gas 5110 to clean the surface of the sample. Exposures to reactive gas 5110 can occur for relatively short times. For example, in some embodiments, sample 180 can be exposed to reactive gas 5110 for periods of 48 hours or less (e.g., 36 hours or less, 24 hours or less, 12 hours or less, 4 hours or less, 1 hour or less) and/or for periods of one minute or more (e.g., two minutes or more, five minutes or more, ten minutes or more, 20 minutes or more, 30 minutes or more, 40 minutes or more, 50 minutes or more).

It has also been discovered that, surprisingly, in certain embodiments, reactive gas cleaning of sample 180 can be performed during sample imaging. Although the potential exists for particles of reactive gas 5110 to disrupt ion beam 192 (e.g., increasing the spot size of ion beam 192 on sample 180 and potentially reducing the resolution of sample images acquired via exposure of sample 180 to ion beam 192), it has been found that, provided the pressure of reactive gas 5110 is not too large, both cleaning and imaging of sample 180 can be performed at the same time. By cleaning sample 180 during imaging, image aberrations that might otherwise arise from progressive surface contamination during the course of acquiring an image can be reduced and/or eliminated. Further, by delivering reactive gas 5110 to sample 180 during imaging, a contamination-free zone can be established on the surface of sample 180, so that any contaminants (such as hydrocarbon contaminants, for example) that enter the zone are rapidly volatilized and removed from chamber 5000.

In some embodiments, sample cleaning can be performed prior to imaging. For example, sample 180 can be positioned on sample manipulator 140 in chamber 5000, and then exposed to reactive gas 5110 prior to exposure to ion beam 192. As discussed above, surface contaminants on sample 180 react with gas 5110 to produce a variety of volatile products, which can then be pumped out of chamber 5000 through outlet 5120. Following this initial decontamination step, sample 180 can be imaged via exposure of the sample to ion beam 192, with either continuous or intermittent exposure to additional reactive gas 5110. Alternatively, in some embodiments, a sample decontamination procedure similar to the procedure described above can be performed prior to imaging in a region outside chamber 5000 (e.g., an ante-chamber), and then the decontaminated sample can be mounted on sample manipulator 140 and imaged.

In certain embodiments, reactive gas 5110 includes ozone. Ozone can be introduced directly into tube 5080 by gas supply 5070. In some embodiments, gas supply 5070 includes a direct source of ozone gas. In certain embodiments, gas supply 5070 includes an ozone generator. For example, gas supply 5070 can include one or more radiation sources that are configured to generate electromagnetic fields (e.g., ultraviolet radiation). Oxygen gas (e.g., pure oxygen, or a mixture of gases that includes oxygen gas such as air) is introduced into the ultraviolet radiation. The ultraviolet radiation activates and, in some embodiments, ionizes the oxygen gas to produce ozone. In some embodiments, the ozone generator can include a plurality of electrodes. Oxygen gas is introduced into the electrodes, and a relatively high potential difference is applied across at least some of the electrodes to ionize the oxygen gas and form ozone.

In certain embodiments, high intensity radiofrequency (RF) fields generated by a RF field source can be used form an oxygen-based plasma from a gas such as oxygen gas. The field source can be part of an external sample cleaning chamber which is used to pre-clean samples before introduction into chamber 5000. In some embodiments, for example, samples are cleaned first outside chamber 5000 by a plasma (e.g., an oxygen plasma), then introduced into chamber 5000, and cleaned again with ozone one or more times in chamber 5000.

Generally, tubes 5020, 5050, and 5080, and conduit 5030 are formed of materials such as Teflon® and/or stainless steel that are not significantly degraded by reactive gas 5110. In addition, pump 5060 and the chamber pump in fluid communication with chamber 5000 through outlet 5120 are tolerant to exposure to reactive gas 5110.

In some embodiments, reactive gas 5110 can be introduced into chamber 5000 to decontaminate the chamber. For example, prior to using chamber 5000 for sample imaging, reactive gas 5110 can be introduced into the empty chamber for a period of time (e.g., a few hours, such as 1 hour or more, 2 hours or more, 3 hours or more, 5 hours or more, 10 hours or more, 15 hours or more, 20 hours or more, 24 hours or more). A reactive gas 5110 such as ozone can undergo one or more chemical reactions with contaminants adsorbed onto interior surfaces of chamber 5000, generating volatile reaction products which can then be pumped out of chamber 5000 through outlet 5120.

Although this disclosure refers mainly to ion beam sources, in general, the methods and systems disclosed herein can be used with other types of sample imaging beams as well. For example, exposure of a sample to a reactive gas to remove surface contaminants can be used with other types of charged particle beams such as electron beams (e.g., in electron microscopes). Further, although this disclosure refers mainly to gas field ion sources, the methods and systems disclosed herein can be used with other types of ion sources, including other types of gas ion sources, and liquid metal ion sources (e.g., gallium ion beam sources).

In general, as discussed above, ozone gas (and activated and/or ionized derivatives thereof, including oxygen-based plasmas) are effective at reacting with and volatilizing sample surface contaminants such as hydrocarbon contaminants. However, other reactive gases can also be used in addition to, or as alternatives to, ozone. Examples of other suitable reactive gases include oxygen radicals, water (and/or ionized water), hydrogen, protons, and hydride ions.

The rate at which contaminants are removed from sample 180 is dependent, in part, on the flow rate of reactive gas 5110 introduced into chamber 5000. In some embodiments, a flow rate of reactive gas 5110 into chamber 5000 is $10^{-6}$ Torr L s$^{-1}$ or more (e.g., $10^{-5}$ Torr L s$^{-1}$ or more, $10^{-4}$ Torr L s$^{-1}$ or more, $10^{-3}$ Torr L s$^1$ or more, 1031 2 Torr L s$^{-1}$ or more) and/or $10^3$ Torr L s$^{-1}$ or less (e.g., $10^2$ Torr L s$^{-1}$ or less, 10 Torr L s$^{-1}$ or less, 1 Torr L s$^{-1}$ or less).

In general, a pressure of reactive gas 5110 in chamber 5000 can be selected as desired to control a reaction rate of reactive gas 5110 with contaminants on sample 180. In some embodiments, for example, the pressure of reactive gas 5110 in the chamber can be $10^{-8}$ Torr or more (e.g., $10^{-7}$ Torr or more, $10^{-6}$ Torr or more, $10^{-5}$ Torr or more, $10^{-4}$ Torr or more) and/or 100 Torr or less (e.g., 50 Torr or less, 10 Torr or less, 1 Torr or less, 0.1 Torr or less, 0.01 Torr or less).

In certain embodiments, although reactive gas 5110 is introduced into chamber 5000, the overall background pressure in chamber 5000 remains less (e.g., significantly less) than atmospheric pressure. For example, the background pressure in chamber 5000 can be $10^{-5}$ Torr or less (e.g., $10^{-6}$ Torr or less, $10^{-7}$ Torr or less, $10^{-8}$ Torr or less, $10^{-9}$ Torr or less).

Typically, ion beam 192 includes relatively light ions. In some embodiments, for example, ion beam 192 can include one or more different types of noble gas ions such as helium ions, neon ions, and argon ions. In certain embodiments, ion beam 192 can include other types of ions in addition to, or as an alternative to, noble gas ions. Exemplary ions include hydrogen ions and nitrogen ions. In general, the ions in ion beam 192 have a molecular weight of 40 atomic mass units or less (e.g., 30 atomic mass units or less, 20 atomic mass units or less, 15 atomic mass units or less, 10 atomic mass units or less, 4 atomic mass units or less).

A particular advantage of the methods and systems disclosed herein is the applicability of such methods and systems to high magnification, high resolution imaging using ion beams such as helium ion beams. In certain embodiments, for example, a field of view of an image of the sample obtained after and/or during exposure of the sample to a reactive gas to remove contaminants from the sample is 10 microns or less (e.g., 8 microns or less, 6 microns or less, 4 microns or less, 2 microns or less, one micron or less, 750 nm or less, 500 nm or less, 250 nm or less, 100 nm or less, 50 nm or less). In general, the field of view refers to refers to the area of a sample surface that is imaged.

During imaging, a spot size of the ion beam on the surface of sample 180 can be 50 nm or less (e.g., 40 nm or less, 30 nm or less, 20 nm or less, 15 nm or less, 10 nm or less, 8 nm or less, 6 nm or less, 5 nm or less, 4 nm or less, 3 nm or less, 2 nm or less, 1 nm or less). Methods and systems for determining the spot size of the ion beam on sample 180 are disclosed, for example, in U.S. Patent Application Publication No. US 2007/0158558, the entire contents of which are incorporated herein by reference.

Moreover, during imaging, a resolution of an image of sample 180 can be 50 nm or less (e.g., 30 nm or less, 20 nm or less, 10 nm or less, 8 nm or less, 6 nm or less, 5 nm or less, 4 nm or less, 3 nm or less, 2 nm or less, 1 nm or less, 0.5 nm or less, 0.1 nm or less). Methods and systems for determining the resolution of an image are disclosed, for example, in U.S. Patent Application Publication No. US 2007/0158558.

In some embodiments, electronic control system 170 can be configured to analyze particles from sample 180 to identify particular surface contaminants on the sample. For example, prior to exposing sample 180 to reactive gas 5110, sample 180 can be exposed to ion beam 192 to cause particles to leave sample 180. At least some of the particles can be detected by a detector positioned within chamber 5000 (e.g., detector 150, or another detector). Based on the detected particles, electronic control system 170—which is in electrical communication with the detector—can identify certain types of contaminants present on the surface of sample 180. For example, surface contaminants can be identified on the basis of masses, charges, and/or other properties of the detected particles. Electronic control system 170 can then be configured to regulate the flow rate, composition, exposure time, and other properties of reactive gas 5110 to achieve decontamination of the surface of sample 180, prior to and/or during exposure of sample 180 to ion beam 192 to obtain images of sample 180.

In certain embodiments, electronic control system 170 can be configured to generate a first image of sample 180 by exposing the sample to ion beam 192 to generate a plurality of particles that leave the sample, and then detecting the particles with one or more detectors (e.g., detector 150) positioned within chamber 5000. The first image can be generated based on the detected particles. Electronic control system 170 can then analyze the first image to identify the presence of contaminants on sample 180. On the basis of this identification, electronic control system 170 can then be configured to regulate the flow rate, composition, exposure time, and other properties of reactive gas 5110 to achieve decontamination of the surface of sample 180, prior to and/or during exposure of sample 180 to ion beam 192 to obtain subsequent images of the sample with reduced imaging errors.

In some embodiments, sample 180 can be exposed intermittently to reactive gas 5110 during sample imaging (e.g., during exposure of sample 180 to ion beam 192). In general, the exposure times and non-exposure intervals can be selected as desired to provide an appropriate efficiency of decontamination of sample 180, and to avoid significant disturbance to ion beam 192. In certain embodiments, a maximum interval during which the sample is not exposed to reactive gas 5110 during exposure of the sample to ion beam 192 is 5 minutes or less (e.g., 4 minutes or less, 3.5 minutes or less, 3 minutes or less, 2.5 minutes or less, 2 minutes or less, 1.5 minutes or less, 1 minute or less, 0.5 minute or less).

Ion Beam Systems

This section discloses systems and methods for producing ion beams, and detecting particles including secondary electrons and scattered ions that leave a sample of interest due to exposure of the sample to an ion beam. The systems and methods can be used to obtain one or more images of the sample.

Typically, gas ion beams that are used to interrogate samples are produced in multipurpose microscope systems. Microscope systems that use a gas field ion source to generate ions that can be used in sample analysis (e.g., imaging) are referred to as gas field ion microscopes. A gas field ion source is a device that includes an electrically conductive tip (typically having an apex with 10 or fewer atoms) that can be used to ionize neutral gas species to generate ions (e.g., in the form of an ion beam) by bringing the neutral gas species into the vicinity of the electrically conductive tip (e.g., within a distance of about four to five angstroms) while applying a high positive potential (e.g., one kV or more relative to the extractor (see discussion below)) to the apex of the electrically conductive tip.

Figure 2:
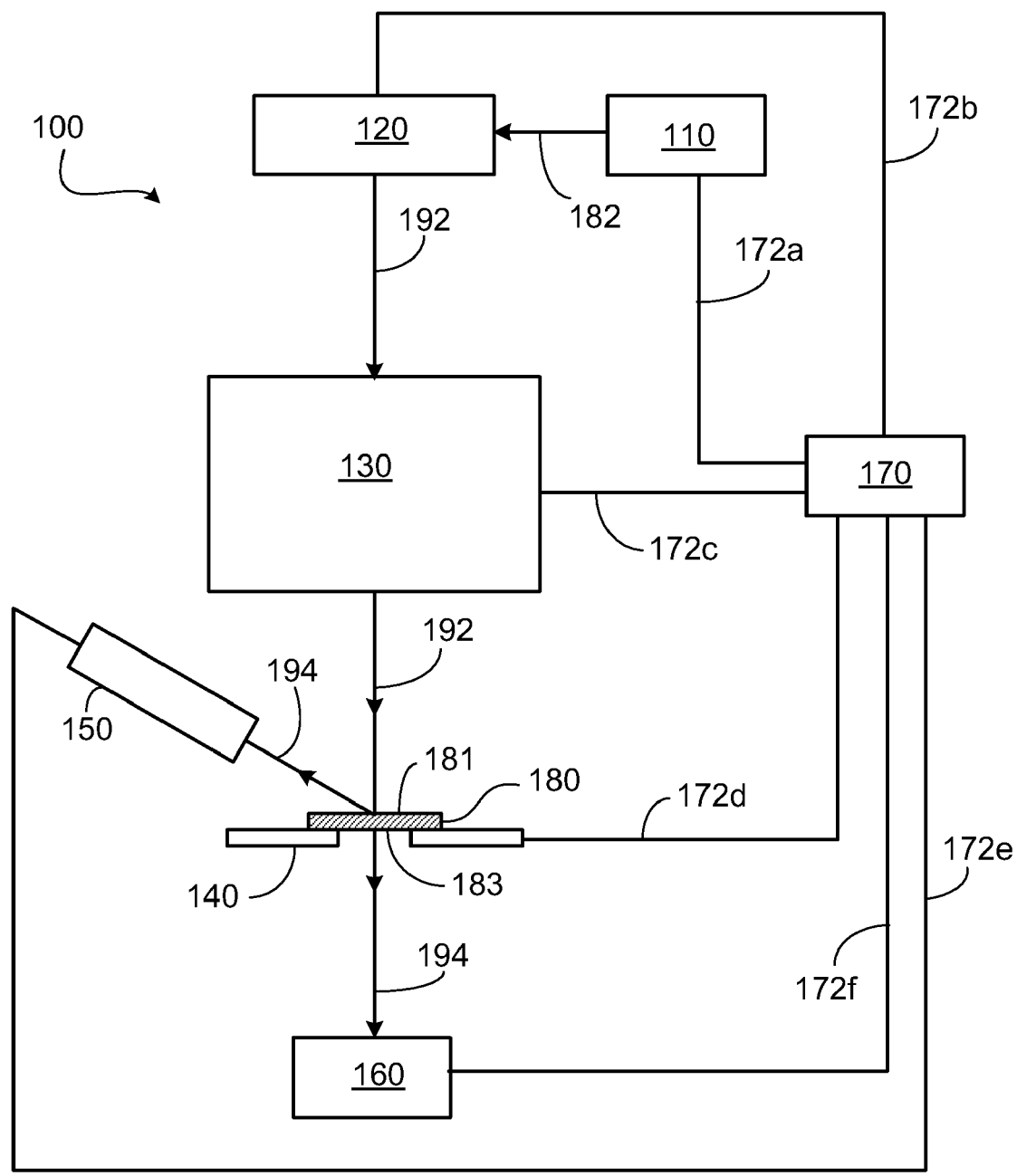
FIG. 2 is a schematic diagram of an ion microscope system.

FIG. 2 shows a schematic diagram of a gas field ion microscope system 100 that includes a gas source 110, a gas field ion source 120, ion optics 130, a sample manipulator 140, a front-side detector 150, a back-side detector 160, and an electronic control system 170 (e.g., an electronic processor, such as a computer) electrically connected to various components of system 100 via communication lines 172a-172f. A sample 180 is positioned in/on sample manipulator 140 between ion optics 130 and detectors 150, 160. During use, an ion beam 192 is directed through ion optics 130 to a surface 181 of sample 180, and particles 194 resulting from the interaction of ion beam 192 with sample 180 are measured by detectors 150 and/or 160.

Figure 3:
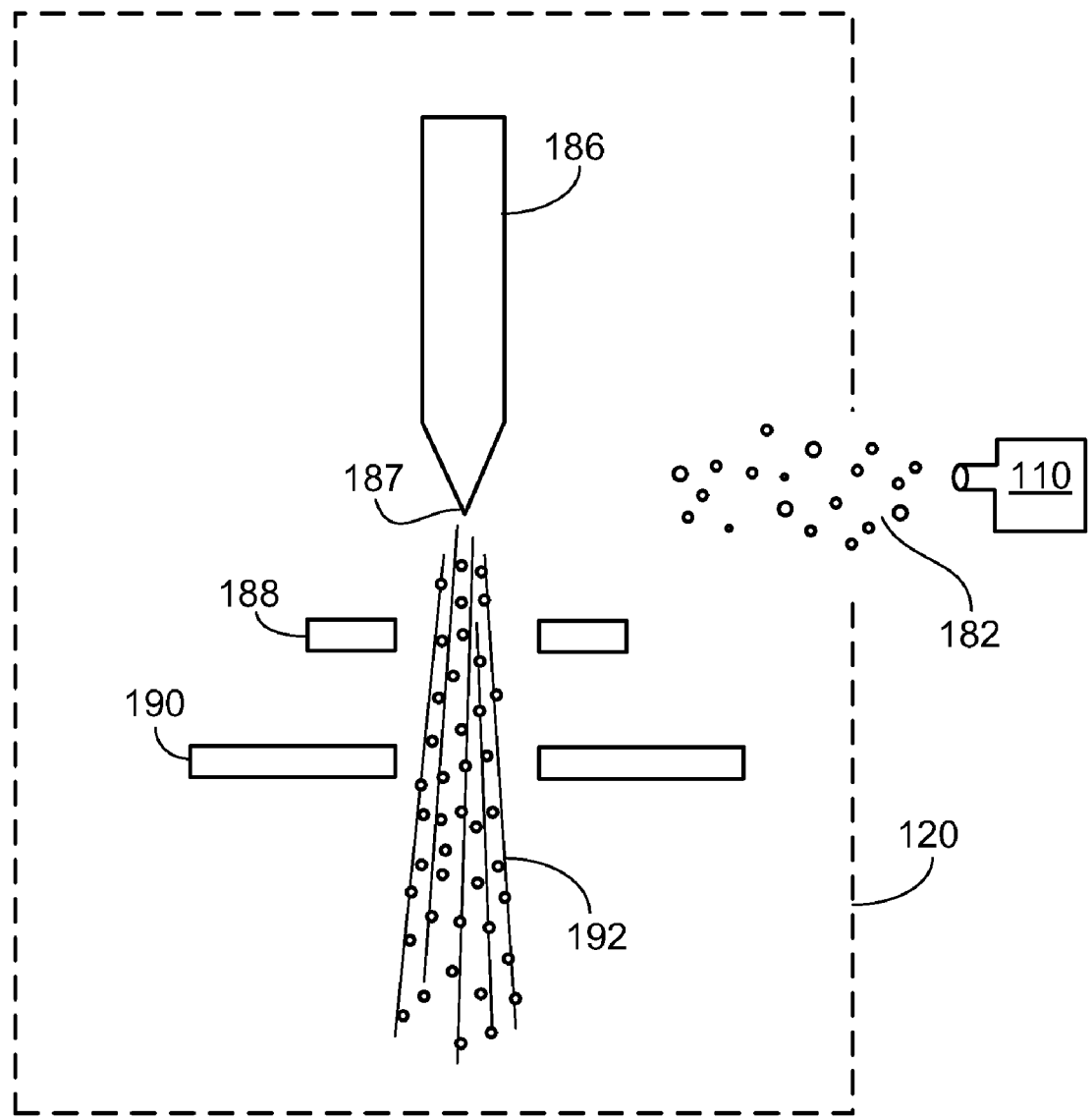
FIG. 3 is a schematic diagram of a gas field ion source.
Like reference symbols in the various drawings indicate like elements.

As shown in FIG. 3, gas source 110 is configured to supply one or more gases 182 to gas field ion source 120. Gas source 110 can be configured to supply the gas(es) at a variety of purities, flow rates, pressures, and temperatures. In general, at least one of the gases supplied by gas source 110 is a noble gas (helium (He), neon (Ne), argon (Ar), krypton (Kr), xenon (Xe)), and ions of the noble gas are desirably the primary constituent in ion beam 192.

Optionally, gas source 110 can supply one or more gases in addition to the noble gas(es); an example of such a gas is nitrogen. Typically, while the additional gas(es) can be present at levels above the level of impurities in the noble gas(es), the additional gas(es) still constitute minority components of the overall gas mixture introduced by gas source 110.

Gas field ion source 120 is configured to receive the one or more gases 182 from gas source 110 and to produce gas ions from gas(es) 182. Gas field ion source 120 includes an electrically conductive tip 186 with a tip apex 187, an extractor 190 and optionally a suppressor 188.

Electrically conductive tip 186 can be formed of various materials. In some embodiments, tip 186 is formed of a metal (e.g., tungsten (W), tantalum (Ta), iridium (Ir), rhenium (Rh), niobium (Nb), platinum (Pt), molybdenum (Mo)). In certain embodiments, electrically conductive tip 186 can be formed of an alloy. In some embodiments, electrically conductive tip 186 can be formed of a different material (e.g., carbon (C)).

During use, tip 186 is biased positively (e.g., approximately 20 kV) with respect to extractor 190, extractor 190 is negatively or positively biased (e.g., from −20 kV to +50 kV) with respect to an external ground, and optional suppressor 188 is biased positively or negatively (e.g., from −5 kV to +5 kV) with respect to tip 186. Because tip 186 is formed of an electrically conductive material, the electric field of tip 186 at tip apex 187 points outward from the surface of tip apex 187. Due to the shape of tip 186, the electric field is strongest in the vicinity of tip apex 187. The strength of the electric field of tip 186 can be adjusted, for example, by changing the positive voltage applied to tip 186. With this configuration, un-ionized gas atoms 182 supplied by gas source 110 are ionized and become positively-charged ions in the vicinity of tip apex 187. The positively-charged ions are simultaneously repelled by positively charged tip 186 and attracted by negatively charged extractor 190 such that the positively-charged ions are directed from tip 186 into ion optics 130 as ion beam 192. Suppressor 188 assists in controlling the overall electric field between tip 186 and extractor 190 and, therefore, the trajectories of the positively-charged ions from tip 186 to ion optics 130. In general, the overall electric field between tip 186 and extractor 190 can be adjusted to control the rate at which positively-charged ions are produced at tip apex 187, and the efficiency with which the positively-charged ions are transported from tip 186 to ion optics 130.

In general, ion optics 130 are configured to direct ion beam 192 onto surface 181 of sample 180. Ion optics 130 can, for example, focus, collimate, deflect, accelerate, and/or decelerate ions in beam 192. Ion optics 130 can also allow only a portion of the ions in ion beam 192 to pass through ion optics 130. Generally, ion optics 130 include a variety of electrostatic and other ion optical elements that are configured as desired. By manipulating the electric field strengths of one or more components (e.g., electrostatic deflectors) in ion optics 130, ion beam 192 can be scanned across surface 181 of sample 180. For example, ion optics 130 can include two deflectors that deflect ion beam 192 in two orthogonal directions. The deflectors can have varying electric field strengths such that ion beam 192 is rastered across a region of surface 181.

When ion beam 192 impinges on sample 180, a variety of different types of particles 194 can be produced. These particles include, for example, secondary electrons, Auger electrons, secondary ions, secondary neutral particles, primary neutral particles, scattered ions and photons (e.g., X-ray photons, IR photons, visible photons, UV photons). Detectors 150 and 160 are positioned and configured to each measure one or more different types of particles resulting from the interaction between ion beam 192 and sample 180. As shown in FIG. 2, detector 150 is positioned to detect particles 194 that originate primarily from surface 181 of sample 180, and detector 160 is positioned to detect particles 194 that emerge primarily from surface 183 of sample 180 (e.g., transmitted particles). In general, any number and configuration of detectors can be used in the microscope systems disclosed herein. In some embodiments, multiple detectors are used, and some of the multiple detectors are configured to measure different types of particles. In certain embodiments, the detectors are configured to provide different information about the same type of particle (e.g., energy of a particle, angular distribution of a given particle, total abundance of a given particle). Optionally, combinations of such detector arrangements can be used.

In general, the information measured by the detectors is used to determine information about sample 180. Typically, this information is determined by obtaining one or more images of sample 180. By rastering ion beam 192 across surface 181, pixel-by-pixel information about sample 180 can be obtained in discrete steps. Detectors 150 and/or 160 can be configured to detect one or more different types of particles 194 at each pixel.

The operation of microscope system 100 is typically controlled via electronic control system 170. For example, electronic control system 170 can be configured to control the gas(es) supplied by gas source 110, the temperature of tip 186, the electrical potential of tip 186, the electrical potential of extractor 190, the electrical potential of suppressor 188, the settings of the components of ion optics 130, the position of sample manipulator 140, and/or the location and settings of detectors 150 and 160. Optionally, one or more of these parameters may be manually controlled (e.g., via a user interface integral with electronic control system 170). Additionally or alternatively, electronic control system 170 can be used (e.g., via an electronic processor, such as a computer) to analyze the information collected by detectors 150 and 160 and to provide information about sample 180 (e.g., topography information, material constituent information, crystalline information, voltage contrast information, optical property information, magnetic information ), which can optionally be in the form of an image, a graph, a table, a spreadsheet, or the like. Typically, electronic control system 170 includes a user interface that features a display or other kind of output device, an input device, and a storage medium.

In certain embodiments, electronic control system 170 can be configured to control various properties of ion beam 192. For example, control system 170 can control a composition of ion beam 192 by regulating the flow of gases into gas field ion source 120. By adjusting various potentials in ion source 120 and ion optics 130, control system 170 can control other properties of ion beam 192 such as the position of the ion beam on sample 180, and the average energy of the incident ions.

In some embodiments, electronic control system 170 can be configured to control additional devices. For example, electronic control system 170 can be configured to regulate a supply (e.g., control flow rate and/or gas composition) of a reactive gas delivered to sample 180 in the vicinity of ion beam 192 to react with and partially or fully volatilize the contaminants, which can then be removed from the chamber.

Detectors 150 and 160 are depicted schematically in FIG. 2, with detector 150 positioned to detect particles from surface 181 of sample 180 (the surface on which the ion beam impinges), and detector 160 positioned to detect particles from surface 183 of sample 180. In general, a wide variety of different detectors can be employed in microscope system 200 to detect different particles, and microscope system 200 can typically include any desired number of detectors. The configuration of the various detector(s) can be selected in accordance with particles to be measured and the measurement conditions. In some embodiments, a spectrally resolved detector can be used. Such detectors are capable of detecting particles of different energy and/or wavelength, and resolving the particles based on the energy and/or wavelength of each detected particle.

Ion beam systems and methods are generally disclosed, for example, in U.S. Patent Application Publication No. US 2007/0158558.

Computer Hardware and Software

In general, any of the methods (or portions thereof, such as control steps) described above can be implemented in computer hardware or software, or a combination of both. The methods can be implemented in computer programs using standard programming techniques following the methods and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The methods or portions thereof can also be implemented as a computer-readable storage medium, configured with a computer program, where the storage medium so configured causes a computer to operate in a specific and predefined manner to perform the functions described herein.

Other Embodiments

Although certain exemplary embodiments have been discussed herein, other embodiments are also possible. In some embodiments, instead of support 5010 supporting reactive gas delivery tube 5020, reactive gas delivery tube 5020 can be supported in another manner. For example, gas delivery tube 5020—which can include a single tube or multiple tubes (e.g., two tubes, three tubes, four tubes, five tubes, or even more tubes) can be connected to a lower surface of the ion column (e.g., ion optics 130), for example, and positioned to deliver reactive gas to the sample.

Other embodiments are in the claims.

What is claimed is:

1. A method, comprising:
   exposing a sample in a chamber to a first gas, wherein the first gas reacts with surface contaminants on the sample to form a second gas;
   removing at least a portion of the second gas from the chamber; and
   exposing the sample to a noble gas ion beam to cause a plurality of particles to leave the sample and detecting at least some of the plurality of particles,
   wherein the noble gas ion beam comprises particles having a molecular weight of 40 atomic mass units or less.

2. The method of claim 1, wherein the first gas is ozone.

3. The method of claim 1, wherein the surface contaminants comprise hydrocarbons.

4. The method of claim 1, wherein a background pressure in the chamber during exposure of the sample to the first gas is less than atmospheric pressure.

5. The method of claim 1, wherein the sample is exposed to the first gas during exposure of the sample to the noble gas ion beam.

6. The method of claim 5, further comprising exposing the sample to the first gas prior to exposing the sample to the noble gas ion beam to form a second gas, and removing at least a portion of the second gas from the chamber.

7. The method of claim 6, wherein the sample is exposed to the first gas in a region outside the chamber prior to exposing the sample to the noble gas ion beam in the chamber.

8. The method of claim 1, wherein the plurality of particles comprise secondary electrons, scattered ions, or noble gas ions.

9. The method of claim 1, wherein the noble gas ion beam comprises particles having a molecular weight of 20 atomic mass units or less.

10. The method of claim 1, further comprising forming the first gas by introducing gas particles into an activation apparatus, and activating the gas particles to form the first gas.

11. The method of claim 1, further comprising producing the noble gas ion beam in a gas field ion source.

12. The method of claim 1, further comprising forming an image of the sample based on the detected particles, wherein a maximum dimension of a field of view of the image is 10 microns or less.

13. The method of claim 1, further comprising, prior to exposing the sample to the first gas:
    exposing the sample to the noble gas ion beam to cause a plurality of particles to leave the sample, detecting at least some of the plurality of particles, and forming an image of the sample based on the detected particles; and
    analyzing the image to identify at least some of the surface contaminants.

14. The method of claim 1, further comprising, prior to exposing the sample to the first gas:
    exposing the sample to the noble gas ion beam to cause a plurality of particles to leave the sample, detecting at least some of the plurality of particles, and identifying at least some of the surface contaminants based on the detected particles.

15. The method of claim 1, further comprising:
    exposing one or more internal surfaces of the chamber to the first gas, wherein the first gas reacts with contaminants on the one or more internal surfaces of the chamber to form a third gas; and
    removing at least a portion of the third gas from the chamber.

16. The method of claim 1, further comprising, before exposing the sample to the first gas:
    forming a plasma, and exposing the sample to the plasma outside the chamber, wherein the plasma reacts with surface contaminants on the sample to form products; and
    removing at least a portion of the products from the sample surface.

17. The method of claim 16, further comprising introducing the sample into the chamber.

18. A method, comprising:
    exposing a sample to a noble gas ion beam to cause a plurality of particles to leave the sample and detecting at least some of the plurality of particles; and
    during exposure of the sample to the noble gas ion beam, exposing the sample to a first gas, wherein the first gas reacts with surface contaminants on the sample to form a second gas, and removing at least a portion of the second gas from the chamber.

19. A method, comprising:
    exposing a sample in a chamber to ozone, wherein the ozone reacts with surface contaminants on the sample to form volatile reaction products;
    removing at least a portion of the volatile reaction products from the chamber; and
    exposing the sample to a helium ion beam to cause a plurality of particles to leave the sample and detecting at least some of the plurality of particles.

* * * * *

UNITED STATES PATENT AND TRADEMARK OFFICE
CERTIFICATE OF CORRECTION

| | | |
|---|---|---|
| PATENT NO. | : 8,013,300 B2 | Page 1 of 1 |
| APPLICATION NO. | : 12/470316 | |
| DATED | : September 6, 2011 | |
| INVENTOR(S) | : Lewis A. Stern | |

It is certified that error appears in the above-identified patent and that said Letters Patent is hereby corrected as shown below:

<u>First Page, Col. 2 (Other Publications),</u>
Line 2, delete "Technolog.," and insert --Technology.,--

<u>Column 1,</u>
Line 57, delete "an" and insert --can--

<u>Column 7,</u>
Line 47, delete "1031 2" and insert --$10^{-2}$--

<u>Column 11,</u>
Line 32, delete "information )," and insert --information),--

Signed and Sealed this
Eighteenth Day of October, 2011

David J. Kappos
*Director of the United States Patent and Trademark Office*